(12) United States Patent
Buchbinder et al.

(10) Patent No.: US 10,252,956 B2
(45) Date of Patent: Apr. 9, 2019

(54) VISCOSITY MODIFIERS FOR DECREASING THE VISCOSITY OF IONIC LIQUIDS

(71) Applicant: UOP LLC, Des Plaines, IL (US)

(72) Inventors: Avram M. Buchbinder, Chicago, IL (US); Erin M. Broderick, Arlington Heights, IL (US); Susie C. Martins, Carol Stream, IL (US); Alakananda Bhattacharyya, Glen Ellyn, IL (US); Stuart Smith, Lake Zurich, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 16/035,851

(22) Filed: Jul. 16, 2018

(65) Prior Publication Data
US 2018/0319718 A1  Nov. 8, 2018

Related U.S. Application Data

(63) Continuation of application No. 14/568,698, filed on Dec. 12, 2014, now Pat. No. 10,023,508.

(51) Int. Cl.
*C07C 2/58* (2006.01)
*C07C 2/62* (2006.01)
*C07C 2/60* (2006.01)
*B01J 31/02* (2006.01)

(52) U.S. Cl.
CPC .............. *C07C 2/60* (2013.01); *B01J 31/0277* (2013.01); *C07C 2527/125* (2013.01); *C07C 2531/02* (2013.01)

(58) Field of Classification Search
CPC .................................... C07C 2/60; C07C 9/21
USPC .................................................. 585/722, 727
See application file for complete search history.

(56) References Cited

U.S. PATENT DOCUMENTS

2015/0315103 A1\* 11/2015 Klusener ................... C07C 2/58
585/719

\* cited by examiner

*Primary Examiner* — Thuan D Dang

(57) ABSTRACT

A process utilizing an ionic liquid is described. The process includes contacting a hydrocarbon feed with an ionic liquid component, the ionic liquid component comprising a mixture of a first ionic liquid and a viscosity modifier, wherein a viscosity of the ionic liquid component is at least about 10% less than a viscosity of the first ionic liquid.

4 Claims, 4 Drawing Sheets

VISCOSITY MODIFIERS FOR DECREASING THE VISCOSITY OF IONIC LIQUIDS

CROSS-REFERENCE TO RELATED APPLICATION

This application is a Continuation of copending application Ser. No. 14/568,698 filed Dec. 12, 2014, the contents of which cited application are hereby incorporated by reference in its entirety.

BACKGROUND OF THE INVENTION

In processes utilizing ionic liquids as catalysts, extraction solvents, or adsorbents, the high viscosity of the ionic liquids (IL) often results in mass transfer limitations on the process. For instance, in motor fuel alkylation using heptachloroaluminate ionic liquids, high shear mixing may be necessary to produce sufficient surface area to overcome the mass transfer resistance. This is especially evident for high viscosity ionic liquids such as some phosphonium ionic liquids, which otherwise have particular selectivity advantages over nitrogen-based ionic liquids. The high shear mixing leads to droplets of ionic liquid being dispersed in the hydrocarbon phase. Small droplets are more difficult to separate after reaction than larger droplets.

Similar mass transfer resistance is expected in other ionic liquid processes, such as alkane disproportionation and reverse disproportionation, gas separation using ionic liquids (such as $CO_2$ and $H_2S$ separation from $CH_4$), and extractions using ionic liquids, such as denitrogenation of heavy feedstocks.

Therefore, there is a need for methods for decreasing the mass transfer resistance of the ionic liquid while not requiring significant decrease in droplet size.

SUMMARY OF THE INVENTION

One aspect of the invention involves a process utilizing an ionic liquid. In one embodiment, the process includes contacting a hydrocarbon feed with an ionic liquid component, the ionic liquid component comprising a mixture of a first unsupported ionic liquid and a viscosity modifier, wherein a viscosity of the ionic liquid component is at least about 10% less than a viscosity of the first unsupported ionic liquid.

DETAILED DESCRIPTION OF THE INVENTION

Figure 1:
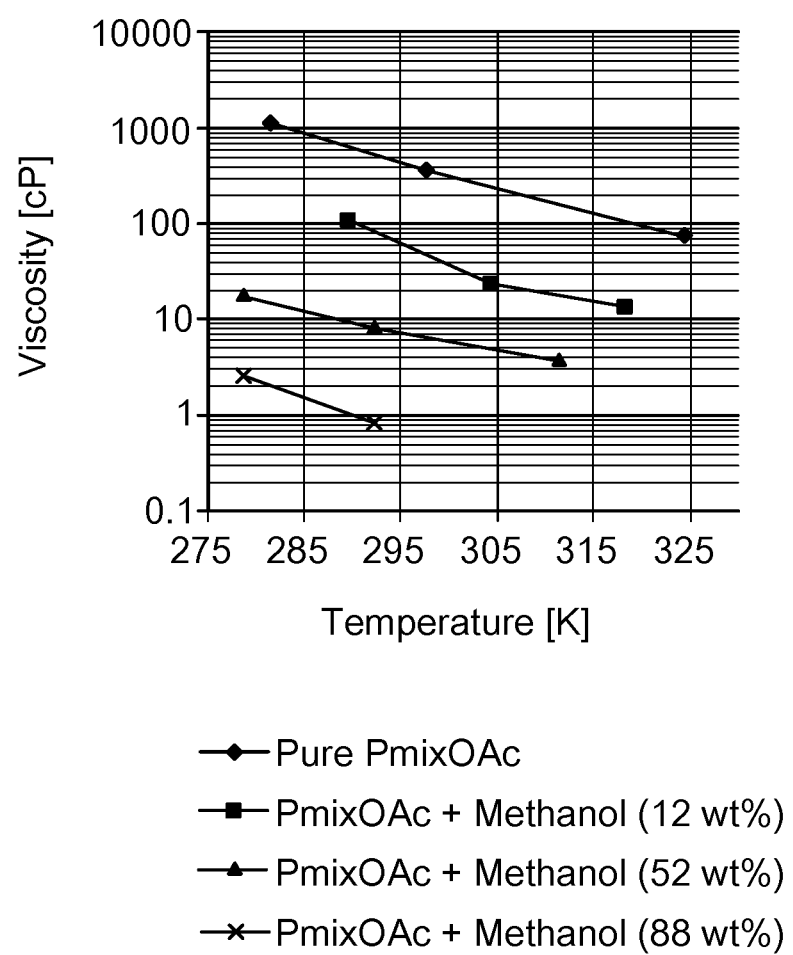
FIG. 1 shows the viscosity of tris(propyl/butyl)methylphosphonium acetate with varying amounts of methanol as a function of temperature.

Rather than decreasing mass transfer resistance by reducing droplet size using mechanical methods (high shear), this invention reduces mass transfer resistance (and increases observed reaction rate) by adding a viscosity modifier to the ionic liquid. The viscosity modifiers are targeted to decrease the viscosity of the ionic liquid, and therefore increase the diffusivity of the reactants in the ionic liquid. An alternative or additional theory for the effectiveness of the viscosity modifiers in these circumstances is increased solubility of the reactants.

In order to decrease the viscosity of the ionic liquid, the ionic liquid itself could be changed or modified, the process temperature could be increased, or a viscosity modifier could be used. Changing the ionic liquid could result in losses of desired properties such as high reaction selectivity, solubility, or thermal stability. Similarly, raising the temperature to achieve lower viscosity would decrease product octane in the case of motor fuel alkylation, and would have similar negative effects in other processes due to intrinsic reaction or absorption rates and selectivities changing with temperature.

One case in the open literature suggests using ionic liquids as additives to traditional sulfuric acid or triflic acid alkylation. However, in that case, the ionic liquid was used to change the properties of the conventional acid, and the viscosity was not shown as a reason for the observed improvements. Cong et al., Isobutane/2-Butene Alkylation Catalyzed by Strong Acids in the Presence of Ionic Liquid Additives, *Petrol. Sci. & Tech.*, 32, 1981-1987, 2014.

In some embodiments, the addition of the viscosity modifier to the ionic liquid provides increased apparent reaction rates and/or improved selectivities.

In some embodiments, the amount of the viscosity modifier added will change during the process. For example, a certain viscosity range will be selected to operate the process. However, as the process continues, the viscosity of the ionic liquid will change, for instance as the amount of conjunct polymer in the ionic liquid increases, leading to increased viscosity of the ionic liquid. By conjunct polymer, we mean the materials containing olefinic, conjugated and cyclic hydrocarbons that form as a byproduct of various hydrocarbon conversion processes, including but not limited to alkylation, oligomerization, isomerization, disproportionation, and reverse disproportionation. In that situation, the amount of viscosity modifier could be increased so that the viscosity of the ionic liquid component remains within the target viscosity range. Using an additive thus provides flexibility compared to simply selecting an ionic liquid in the target range.

In some embodiments, all or a portion of the viscosity modifier will remain with the ionic liquid and can be recovered with the ionic liquid. In other embodiments, all or a portion of the viscosity modifier will remain with the hydrocarbon. It can be recovered using a separation process, such as fractionation.

In some embodiments, the use of the viscosity modifier allows the process to be operated at a lower temperature. In some embodiments, operating at lower temperatures will result in improved selectivity.

In some embodiments, the use of the viscosity modifier results in increased diffusivity of the reactants allowing the use of larger droplets while maintaining a similar effective rate constant. Recovery of larger droplets generally requires a smaller gravity settler or can avoid the use of specialized separation equipment that may be necessary to recover smaller droplets.

The first ionic liquid can be any ionic liquid. The ionic liquid comprises an organic cation and an anion. Suitable cations include, but are not limited to, nitrogen-containing cations and phosphorus-containing cations. The first ionic liquid can comprise phosphonium based ionic liquids, pyridinium based ionic liquids, imidazolium based ionic liquids, ammonium based ionic liquids, pyrrolidinium based ionic liquids, and lactamium based ionic liquids. Lactamium based ionic liquids comprise cyclic amides. Lactamium ionic liquids include, but are not limited to, those described in U.S. Pat. No. 8,709,236, U.S. application Ser. No. 14/271,308, entitled Synthesis of Lactam Based Ionic Liquids, filed May 6, 2014, and U.S. application Ser. No. 14/271,319, entitled Synthesis of N-Derivatized Lactam Based Ionic Liquids, filed May 6, 2014, which are incorporated by reference. Ammonium based ionic liquids include trialkyl and tetraalkyl ammonium based ionic liquids.

For alkylation, the anion can be derived from halides, typically halometallates, and combinations thereof. The anion is typically derived from metal and nonmetal halides, such as metal and nonmetal chlorides, bromides, iodides, fluorides, or combinations thereof. Combinations of halides include, but are not limited to, mixtures of two or more metal or nonmetal halides (e.g., $AlCl_4^-$ and $BF_4^-$), and mixtures of two or more halides with a single metal or nonmetal (e.g., $AlCl_3Br^-$). In some embodiments, the metal is aluminum, with the mole fraction of aluminum ranging from $0<Al<0.25$ in the anion. Suitable anions include, but are not limited to, $AlCl_4^-$, $Al_2Cl_7^-$, $Al_3Cl_{10}^-$, $AlCl_3Br^-$, $Al_2Cl_6Br^-$, $Al_3Cl_9Br^-$, $AlBr_4^-$, $Al_2Br_7^-$, $Al_3Br_{10}^-$, $GaCl_4^-$, $Ga_2Cl_7^-$, $Ga_3Cl_{10}^-$, $GaCl_3Br^-$, $Ga_2Cl_6Br^-$, $Ga_3Cl_9Br^-$, $CuCl_2^-$, or $Cu_2Cl_3^-$. For gas adsorption and extractions, other anions can be used.

The ionic liquid typically has a kinematic viscosity in a range of about 10 to about 1500 centistokes at 25° C., or in a range of about 80 to about 250 centistokes at 25° C., or a kinematic viscosity in a range of about 5 to about 400 centistokes at 38° C., or in a range of about 40 to about 140 centistokes at 38° C.

The viscosity of the ionic liquid component, which includes the ionic liquid and the viscosity modifier, is at least about 10% less than the viscosity of the first ionic liquid, or at least about 15% less, or at least about 20% less, or at least about 30% less, or at least about 40% less, or at least about 50% less. The viscosity difference is defined by a viscosity measurement of the ionic liquid component and the ionic liquid at the same temperature. The ionic liquid component, which includes the ionic liquid and the viscosity modifier, typically has a kinematic viscosity of about 1 to about 1350 centistokes at 25° C., or about 50 to about 250 centistokes at 25° C., or about 70 to about 250 centistokes at 25° C., or about 50 to about 225 centistokes at 25° C., or about 50 to about 100 centistokes at 25° C., or a kinematic viscosity in a range of about 0.5 to about 250 centistokes at 38° C., or about 25 to about 160 centistokes at 38° C., or about 25 to about 70 centistokes at 38° C.

The ionic liquid component can be a catalyst in a hydrocarbon conversion process, a solvent in a hydrocarbon conversion process, a solvent in an extraction process, or an adsorbent in an adsorption process. Suitable hydrocarbon conversion processes include, but are not limited to, alkylation, isomerization, oligomerization, disproportionation, and reverse disproportionation.

The viscosity modifier may be almost any molecular compound, salt, dissolved gas or another ionic liquid that has lower viscosity than the original ionic liquid or results in lower viscosity when used as a viscosity modifier. Suitable viscosity modifiers, include, but are not limited to, alcohols, amines, siloxanes, ethers, haloalkanes, aromatics, alkylaromatics, halogenated aromatics, substituted aromatics, substituted alkylaromatics, tetraalkyl silanes, chloro-alkyl silanes, cyclic amides, alkylated amides, halogenated methanes, imides, pyrophosphate salts, polysilicic acids, phosphines, alkyl phosphines, thioethers, nitriles, mineral acids, and carboxylic acids, as well as a second ionic liquid having a viscosity at least about 10% less than the viscosity of the first ionic liquid. The viscosity modifier may also be the conjugate acid of the anion of the first ionic liquid or the second ionic liquid. Alcohols include, but are not limited to, methanol, ethanol, propanol, isopropanol, butanol, and hexanol. Amines include, but are not limited to, trimethylamine, triethylamine, and pyrrolidine. Siloxanes include, but are not limited to, hexamethyldisiloxane. Ethers include, but are not limited to, diethyl ether, tetrahydrofuran and dioxane. Haloalkanes include, but are not limited to, hexachloroethane, chloroethane and bromoethane, hydrofluorocarbons and chlorofluorocarbons. Aromatics include, but are not limited to, benzene. Alkylaromatics include, but are not limited to, toluene, xylene, ethylbenzene, trimethylbenzenes, tetramethylbenzenes, pentamethylbenzenes, hexamethylbenzene, diethylbenzenes, ethyl toluenes, and dimethyl-ethylbenzenes. Halogenated aromatics include, but are not limited to, chlorobenzene, bromobenzene, iodobenzene, fluorobenzene, dibromobenzenes, dichlorobenzenes, chlorotoluenes, dichlorotoluenes, and trichlorotoluenes. Substituted aromatics include, but are not limited to, anisole, and acetophenone. Tetraalkyl silanes include, but are not limited to, tetramethylsilane. Chloro-alkyl silanes include, but are not limited to, chloro-trialkyl silanes such as chlorotriethylsilane, dichlorodialkyl silanes, such as dichlorodiethylsilane and trichloroalkyl silanes such as trichloro-octyl silane. Cyclic amides include, but are not limited to, ε-caprolactam and derivatives of ε-caprolactam, δ-valerolactam and derivatives of δ-valerolactam, and N-methylpyrrolidone and derivatives of N-methylpyrrolidone. Alkylated amides include, but are not limited to, N,N-dimethylacetamide and N,N-dimethylbenzamide. Halogenated methanes include, but are not limited to, dichloromethane, chloromethane, chloroform, bromoform, dibromomethane, fluoromethane, difluoromethane, trifluoromethane, and chlorofluoromethane. Imides include, but are not limited to, succinimide and phthalimide. Pyrophosphate salts include, but are not limited to, metal pyrophosphates and pyrophosphate ionic liquids. Polysilicic acids include, but are not limited to, sodium silicates treated with an acid. Phosphines include, but are not limited to, trialkyl silanes such as triethyl silane, tributyl silane or methyl diphenyl silane and their conjugate acids. Thioethers include, but are not limited to, dimethylsulfide, diethyl sulfide, methyl phenyl sulfide, and tetrahydrothiophene. Nitriles include, but are not limited to, acetonitrile, propylnitrile and benzonitrile. Mineral acids include, but are not limited to, hydrofluoric acid, hydrochloric acid, hydrobromic acid, hydroiodic acid, phosphoric acid, nitric acid, and sulfuric acid. Carboxylic acids include, but are not limited to, formic acid, acetic acid, ethanoic acid, propanoic acid, hexanoic acid and benzoic acid.

Specifically for motor fuel alkylation or other processes requiring the use of heptachloroaluminate or similar ILs, the viscosity modifier needs to be non-reactive. The viscosity modifier should not quench the acidity of the ionic liquid. Many reactants such as water, alcohols, mono- di- and tri-substituted amines, siloxanes, nitriles, and ethers containing protons or free nitrogen or oxygen-based lone-pairs do not meet this criteria (although these would be appropriate viscosity modifiers for other processes). These compounds either have Lewis basic function and coordinate the aluminum in the chloroaluminate catalyst or can act as a Brönsted base and hydrolyze the aluminum. Additionally, the viscosity modifier should not be significantly susceptible to alkylation. This criterion may exclude the use of simple aromatics such as benzene or toluene. Such aromatics may be used if the product is easily removed (for instance by distillation) or if the product also reduces the viscosity of the ionic liquid, or is limited in the extent of reaction such that it does not substantially increase the viscosity of the ionic liquid and does not consume a significant amount of reactant. The viscosity modifier could be limited in the extent of reaction either due to the reaction being limited by equilibrium or due to a reaction which is slow compared to the feed rate of the reactants.

In the case of motor-fuel alkylation, the viscosity modifiers are chosen to allow recovery and recycle either by choosing a viscosity modifier with little or no solubility in the hydrocarbon or with a boiling point that allows recycle of the viscosity modifier with isobutane, or separation from the alkylate product by distillation. Suitable viscosity modifiers for motor fuel alkylation include halogenated aromatics, highly substituted alkylaromatics, tetraalkyl silanes, chloro-alkyl silanes, cyclic amides, halogenated methanes, imides, pyrophosphate salts, other mineral acids, phosphines, and lower viscosity ionic liquids.

In some embodiments, the viscosity modifier is more soluble in the ionic liquid phase than in the hydrocarbon feed. In some embodiments, it has a partition coefficient (defined as the concentration of the viscosity modifier in the hydrocarbon feed divided by the concentration in the ionic liquid component) less than about 0.05 by mass. Viscosity modifiers that are more soluble in the ionic liquid phase than in hydrocarbon feed are preferable because downstream separation from the hydrocarbon product is not required or can be accomplished more easily.

The viscosity modifier is typically present in an amount less than about 40 mol % of the ionic liquid component, or less than about 35 mol %, or less than about 30 mol % or less than about 25 mol %, or less than about 20 mol %, or less than about 15 mol %, or less than about 10 mol %, or less than about 5 mol %.

In some embodiments, the viscosity modifier is a second ionic liquid. When the viscosity modifier is a second ionic liquid, the viscosity of the second ionic liquid is at least about 10% less than the viscosity of the first ionic liquid, or at least about 15% less, or at least about 20% less, or at least about 30% less, or at least about 40% less, or at least about 50% less. Here, the viscosity difference is defined by a viscosity measurement of the two ionic liquids at the same temperature. The viscosity measurement is preferably made in a temperature range of −20° C. to 100° C., or more preferably in the temperature range of 10° C. to 60° C. or even more preferably in the range of 20° C. to 40° C.

Suitable second ionic liquids include, but are not limited to, phosphonium based ionic liquids, pyridinium based ionic liquids, imidazolium based ionic liquids, ammonium based ionic liquids, pyrrolidinium based ionic liquids, and lactamium based ionic liquids. In some embodiments, the second ionic liquid is an imidazolium based ionic liquid, such as, methylimidazolium based ionic liquids, ethylimidazolium based ionic liquids, propylimidazolium based ionic liquids and butylimidazolium based ionic liquids. In one embodiment, the second ionic liquid is a 1-butyl-3-methylimidazolium based ionic liquid. In some embodiments, the second ionic liquid is an ammonium based ionic liquid, such as a trialkyl or tetraalkyl ammonium based ionic liquid. In some embodiments, the second ionic liquid is a triethyl ammonium based ionic liquid. In some embodiments, the second ionic liquid is a phosphonium based ionic liquid, such as a tetraalkylphosphonium based ionic liquid. In some embodiments, the anion of the second ionic liquid is heptachloroaluminate.

In some embodiments, when the viscosity modifier is the second ionic liquid, it can have the same anion as the first ionic liquid, such as the $Al_2Cl_7^-$ anion. When the viscosity modifier is the second ionic liquid, the second ionic liquid typically has a viscosity in a range of about 10 to about 150 centistokes at 25° C., or in a range of about 10 to about 90 centistokes at 25° C., or in a range of about 10 to about 60 centistokes at 25° C., or in a range of about 10 to about 30 centistokes at 25° C.

In some embodiments, when the viscosity modifier is the second ionic liquid, the anion is the same as the anion of the first ionic liquid.

In some embodiments, the ionic liquid component is a catalyst in an alkylation process, the first ionic liquid is a phosphonium based ionic liquid, and the viscosity modifier is at least one of the halogenated aromatic, the substituted alkylaromatic, the tetraalkyl silane, the chloro-alkyl silane, the cyclic amide, the alkylated amide, the halogenated methane, the imide, the pyrophosphate salt, and the second ionic liquid. In some embodiments, the viscosity modifier is the second ionic liquid. In some embodiments, the viscosity modifier is an imidazolium based ionic liquid, ammonium based ionic liquid, pyrrolidinium based ionic liquid, or another phosphonium based ionic liquid.

In some embodiments, the ionic liquid component is a catalyst in an alkylation process, the first ionic liquid is a lactamium based ionic liquid, and the viscosity modifier is at least one of the halogenated aromatic, the substituted alkylaromatic, the tetraalkyl silane, the chloro-alkyl silane, the cyclic amide, the alkylated amide, the halogenated methane, the imide, the pyrophosphate salt, and the second ionic liquid. In some embodiments, the viscosity modifier is the second ionic liquid. In some embodiments, the viscosity modifier is another lactamium based ionic liquid, an imidazolium based ionic liquid, a pyrrolidinium based ionic liquid, an ammonium based ionic liquid, or phosphonium based ionic liquid.

Viscosity modifiers may have non-linear effect on viscosity. This has been seen previously in ionic liquids tested for $CO_2$ absorption. FIG. 1 shows this phenomenon in the effect of adding methanol to tris(propyl/butyl)methylphosphonium acetate (PmixOAc) on viscosity.

Figure 2:
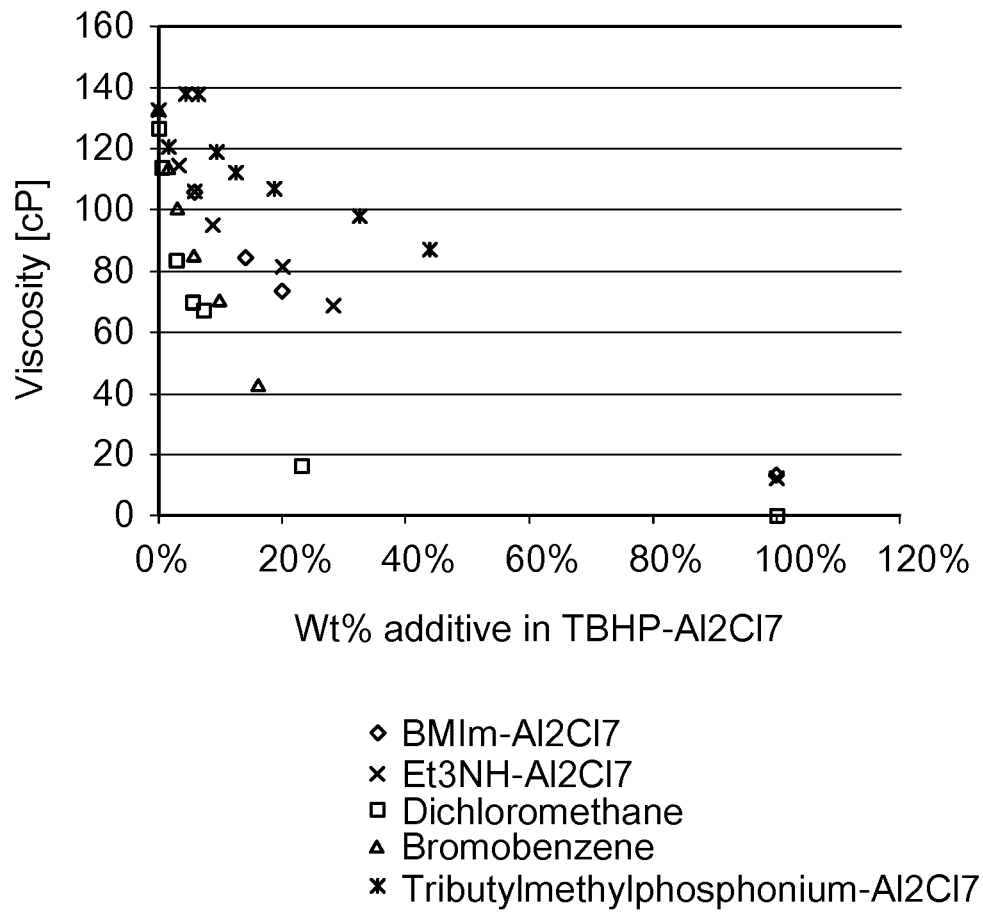
FIG. 2 illustrates the viscosity of mixtures of tributylhexylphosphonium heptachloroaluminate (TBHP-$Al_2Cl_7$) IL with several viscosity modifiers as a function of the weight % of the viscosity modifier.
Figure 3:
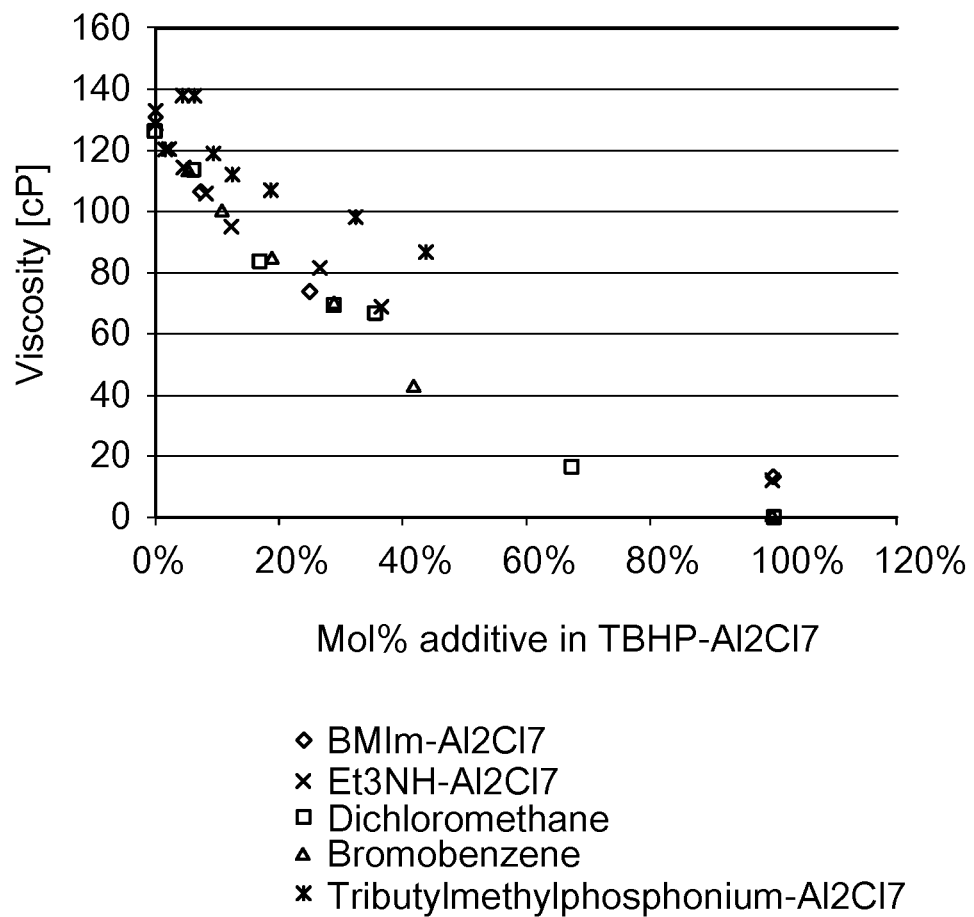
FIG. 3 illustrates the viscosity of mixtures of tributylhexylphosphonium heptachloroaluminate (TBHP-$Al_2Cl_7$) IL with several viscosity modifiers as a function of the mol % of the viscosity modifier.

The dynamic viscosity of mixtures of tributylhexylphosphonium heptachloroaluminate (TBHP-$Al_2Cl_7$) IL with several viscosity modifiers was measured at room temperature (23-26° C.). The results of these measurements are shown in FIG. 2 as a function of viscosity modifier weight % and in FIG. 3 as a function of viscosity modifier mole %. BMIm is 1-butyl-3-methylimidazolium, $Et_3NH$ is triethylammonium.

FIG. 2 shows a non-linear effect of viscosity modifier wt % on viscosity. From the data in FIG. 3, it appears that viscosity of the mixture is simply a linear function of the number of moles of viscosity modifier added (at less than about 30 mol % viscosity modifier concentration). The slope of this relationship is the same unless the viscosity modifier is another phosphonium ionic liquid. One theory is that the viscosity modifier interferes with an inter-ion interaction and thus decreases viscosity. In practice, this implies that the identity of the viscosity modifier is not important for its effect on decreasing viscosity, and should be chosen based on other factors such as molar volume, density and process compatibility. By targeting ionic liquid viscosity modifiers with low molar volume, the concentration of the preferred ionic liquid will be higher, as would the concentration of active sites. Such low-molar volume ionic liquids may include trialkyl and tetra-alkyl ammonium ionic liquids with $C_1$-$C_2$ side chains, and imidazolium, pyridinium, and other nitrogen heterocycle ionic liquids with one or two methyl or ethyl side chains.

Example 1

Two viscosity modifiers (BMIm-$Al_2Cl_7$ and dichloromethane) were tested in isobutane alkylation with 2-butenes, using TBHP-$Al_2Cl_7$ as the primary catalyst. About 8 g of ionic liquid and viscosity modifier was loaded in a 300 cc autoclave and with about 0.24 g 2-chlorobutane (used to activate the catalyst). The autoclave was fitted with a 1.25" Cowles-type impeller. After pressurizing the reactor, While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

TABLE 1

| Ionic liquid component | Impeller diameter (inches) | Mixing time (min) | Butenes conversion | Isobutane/butene mol ratio in feed | $C_5$+ Yield* | Research octane (calc'd) | $C_8$ Sel** | $C_9$+ Sel** | $C_{5-7}$ Sel** | Trimethyl pentane/dimethylhexane ratio in product |
|---|---|---|---|---|---|---|---|---|---|---|
| 1A) TBHP-$Al_2Cl_7$ | 1.25 | 2.5 | 83% | 10.7 | 1.80 | 92.5 | 54 | 30 | 16 | 18.0 |
| 1B) TBHP-$Al_2Cl_7$ | 1.25 | 2.5 | 65% | 11.0 | 1.77 | 92.0 | 54 | 32 | 14 | 18.0 |
| 2) TBHP-$Al_2Cl_7$ | 1.5 | 2.8 | 100% | 11.3 | 2.13 | 95.0 | 66 | 16 | 19 | 17.5 |
| 3) BMIM-$Al_2Cl_7$ | 1.25 | 2.5 | 100% | 10.8 | 2.15 | 95.5 | 78 | 7 | 15 | 11.6 |
| 4) 6 wt % BMIM-$Al_2Cl_7$, 94 wt % TBHP-$Al_2Cl_7$ | 1.25 | 2.5 | 100% | 10.7 | 2.06 | 94.6 | 63 | 19 | 18 | 19.3 |
| 5) 20 wt % BMIM-$Al_2Cl_7$, 80 wt % TBHP-$Al_2Cl_7$ | 1.25 | 2.5 | 100% | 10.8 | 2.12 | 95.7 | 74 | 10 | 16 | 14.6 |
| 6) TBHP-$Al_2Cl_7$ with 4 wt % dichloromethane as additive | 1.25 | 2.5 | 100% | 13.6 | 2.13 | 94.7 | 63 | 18 | 19 | 20.5 |

*weight of $C_5$+ products/weight of olefin feed
**as percentage of $C_5$+ products 80 g of isobutane was charged and mixed to ensure breakdown of 2-chlorobutane. Reaction was initiated by addition of a mixture of 8 g of 2-butenes over the course of 2.5 minutes. The mixture was allowed to settle and the hydrocarbon was analyzed by GC. Table 1 shows butenes conversion as a function of mixing time for these experiments. Pure BMIM-$Al_2Cl_7$ (example 3), as well as 6 wt % or 20% BMIm mixtures with TBHP (examples 4 and 5), and 4% dichloromethane mixture with TBHP (example 6) all result in 100% conversion of butenes after 2.5 minutes. However, TBHP IL alone results in 65- and 83° %/conversion after 2.5 minutes in replicate tests (examples 1A-1B) with lower octane and $C_8$ selectivities than the examples that include a viscosity modifier. This data shows that there is a positive effect of viscosity modifier on reaction rate. As a comparison, TBHP was also tested using a larger 1.5" impeller (example 2) which generates smaller droplets (more surface area). With the 1.5" impeller, 100% conversion of butenes was observed.

Figure 4:
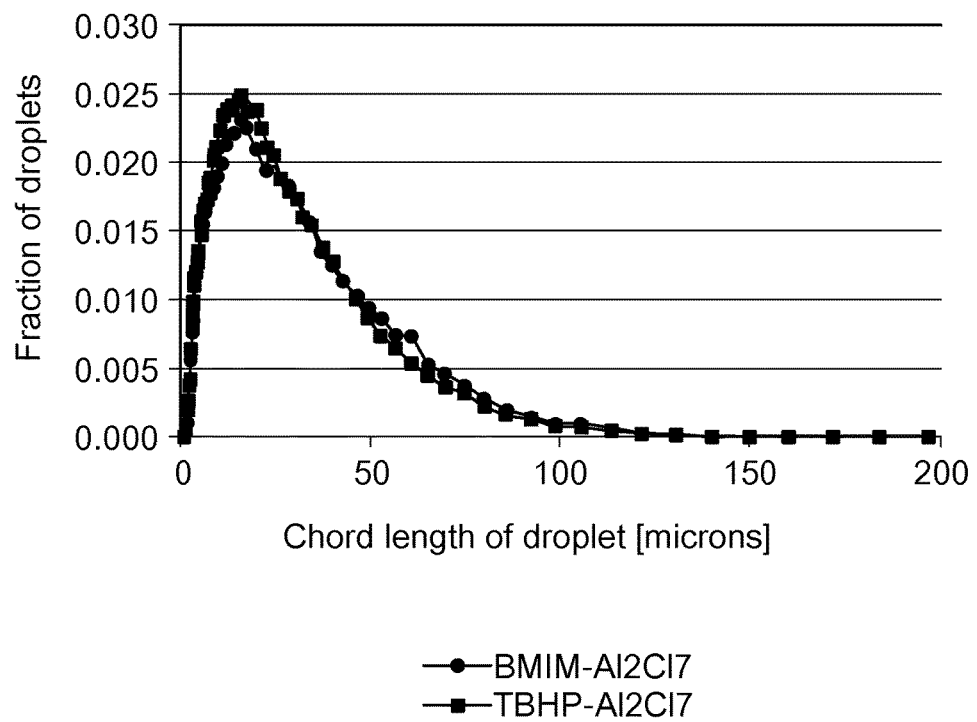
FIG. 4 shows the droplet size distributions for two ionic liquids under similar mixing conditions.

Furthermore, droplet size distributions were measured for both TBHP IL and BMIm IL under similar mixing conditions. The IL was loaded in a 300 mL vessel along with n-octane using an IL volume fraction of 0.1. The contents were mixed using a 1.25 inch Cowles impeller at 1700 rotations per minute and 25° C. Droplet chord lengths were determined using a focused beam reflectance monitor. No significant difference in droplet size was observed (FIG. 4), implying that the improvement in rate is likely due to the difference in viscosity (or possibly solubility) imparted by the viscosity modifier.

What is claimed is:

1. A process utilizing an ionic liquid comprising:
contacting a hydrocarbon feed with an ionic liquid component having a kinematic viscosity in a range of about 50 to about 250 centistokes at 25° C., the ionic liquid component comprising a mixture of a first unsupported ionic liquid comprising a phosphonium based ionic liquid, a pyridinium based ionic liquid, an imidazolium based ionic liquid, an ammonium based ionic liquid, a pyrrolidinium based ionic liquid, and a lactamium based ionic liquid and a viscosity modifier selected from the group consisting of a tetraalkyl silane, a chloro-alkyl silane, a cyclic amide, an alkylated amide, an imide, a phosphine, an alkyl phosphine, a thioether; wherein the viscosity modifier comprises about 15 mol % to about 40 mol % of the ionic liquid component, wherein a viscosity of the ionic liquid component is at least about 10% less than a viscosity of the first ionic liquid, wherein the ionic liquid component is a catalyst in an alkylation process of isoparaffins and olefins, wherein the ionic liquid component is at a temperature of 38° C. or lower.

2. The process of claim 1 wherein the ionic liquid component has a kinematic viscosity in a range of about 25 to about 70 centistokes at 38° C.

3. The process of claim 1 wherein the viscosity modifier is more soluble in the ionic liquid phase than in the hydrocarbon feed.

4. The process of claim 1 wherein an anion of the first ionic liquid comprises Al2Cl7-.

* * * * *